(12) United States Patent
Choung et al.

(10) Patent No.: US 11,534,473 B2
(45) Date of Patent: Dec. 27, 2022

(54) **COMPOSITION FOR PREVENTING OR TREATING HEARING LOSS, CONTAINING *VITIS VINIFERA* LEAF EXTRACT AS ACTIVE INGREDIENT**

(71) Applicant: AJOU UNIVERSITY INDUSTRY-ACADEMIC COOPERATION FOUNDATION, Suwon-si (KR)

(72) Inventors: Yun-Hoon Choung, Seoul (KR); Young Sun Kim, Hwaseong-si (KR); Young-Joon Park, Seoul (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 72 days.

(21) Appl. No.: 16/627,113

(22) PCT Filed: May 30, 2018

(86) PCT No.: PCT/KR2018/006144
§ 371 (c)(1),
(2) Date: Dec. 27, 2019

(87) PCT Pub. No.: WO2019/004610
PCT Pub. Date: Jan. 3, 2019

(65) Prior Publication Data
US 2021/0145919 A1    May 20, 2021

(30) Foreign Application Priority Data
Jun. 28, 2017  (KR) .................. 10-2017-0081827

(51) Int. Cl.
| | | |
|---|---|---|
| A61K 36/87 | (2006.01) |
| A23L 33/105 | (2016.01) |
| A23L 33/00 | (2016.01) |
| A61P 27/16 | (2006.01) |
| A61K 9/00 | (2006.01) |
| A61K 31/05 | (2006.01) |
| A61K 36/16 | (2006.01) |
| A61K 36/258 | (2006.01) |

(52) U.S. Cl.
CPC ............ *A61K 36/87* (2013.01); *A23L 33/105* (2016.08); *A23L 33/40* (2016.08); *A61K 9/0056* (2013.01); *A61K 31/05* (2013.01); *A61K 36/16* (2013.01); *A61K 36/258* (2013.01); *A61P 27/16* (2018.01); *A23V 2002/00* (2013.01); *A61K 2236/333* (2013.01)

(58) Field of Classification Search
CPC ..................................................... A61K 36/00
USPC ......................................................... 424/725
See application file for complete search history.

(56) References Cited

FOREIGN PATENT DOCUMENTS

| | | | |
|---|---|---|---|
| CN | 103202429 | * | 4/2014 |
| JP | 2007-523110 A | | 8/2007 |
| KR | 10-2010-0114349 A | | 10/2010 |

OTHER PUBLICATIONS

Benefits of Vine Leaf on Different Biological Systems Denise S. Lacerda, Pedro C. Costa, Claudia Funchal, Caroline Dani and Rosane Gomez, chapter 6, pp. 125-143, 2016.*
Cho et al., Evaluation of anxiety and depressive levels in tinnitus patients, Korean Journal of audiology, 17, pp. 83-89, 2013.*
Rajesh Singh Pawar, et al., "Ethnopharmacological aspects of resveratrol (a French paradox)—A review", Indigenous Naturalist Journal, 2015, 14-19, vol. 1, No. 2.
Wei Wang, et al., "Distribution of resveratrol and stilbene synthase in young grape plants {*Vitis vinifera* L. cv. Cabernet Sauvignon) and the effect of UV-C on its accumulation", Plant Physiology and Biochemistry, 2010, pp. 142-152, vol. 48.
Michael Seidman, et al., "Effects of resveratrol on acoustic trauma", Otolaryngology-Head and Neck Surgery, Nov. 2003, pp. 463-470, vol. 129, No. 5.
D. Hanci, et al., "Potential protective effect of resveratrol on acoustic trauma: electron microscopy study", European Review for Medical and Pharmacological Sciences, 2016, pp. 3469-3475, vol. 20.
Seung Hwan Lee, "Etiology and Rehabilitation of Sensorineural Hearing Loss", Hanyang Medical. Review, 2015, pp. 55-56, vol. 35.
Alton Meister, "Glutathione Deficiency Produced by Inhibition of its Synthesis, and its Reversal Applications in Research and Therapy" Pharmac. Ther. 1991, pp. 155-194, vol. 51.
Joseph Attias, et al., "Oral Magnesium Intake Reduces Permanent Hearing Loss Induced by Noise Exposure", American Journal of Otolaryngology, Jan.-Feb. 1994, pp. 26-32, vol. 15, No. 1.
Tatsuya Yamasoba, et al., "Ebselen prevents noise-induced excitotoxicity and temporary threshold shift", Neuroscience Letters, 2005, pp. 234-238, vol. 380.
International Search Report for PCT/KR2018/006144 dated Sep. 6, 2018 [PCT/ISA/210].
Written Opinion for PCT/KR2018/006144 dated Sep. 6, 2018 [PCT/ISA/237].
Korean Office Action for 10-2017-0081827 dated Mar. 26, 2018.

* cited by examiner

*Primary Examiner* — Michael V Meller
(74) *Attorney, Agent, or Firm* — Sughrue Mion, PLLC

(57) ABSTRACT

A composition for preventing or treating hearing loss, containing a *Vitis vinifera* leaf extract as an active ingredient, is disclosed. A pharmaceutical composition for preventing or treating hearing loss, containing the extract (a *Vitis vinifera* leaf extract) as an active ingredient, protects auditory hair cells in the cochlea and spiral ganglion cells from damage caused by noise and the like and effectively reduces the hearing threshold measured in the auditory nerves, thereby being usable as an agent for preventing or treating hearing loss.

5 Claims, 8 Drawing Sheets
(7 of 8 Drawing Sheet(s) Filed in Color)

COMPOSITION FOR PREVENTING OR TREATING HEARING LOSS, CONTAINING *VITIS VINIFERA* LEAF EXTRACT AS ACTIVE INGREDIENT

CROSS REFERENCE TO RELATED APPLICATIONS

This application is a National Stage of International Application No. PCT/KR2018/006144, filed on May 30, 2018, which claims priority from Korean Patent Application No. 10-2017-0081827, filed on Jun. 28, 2017.

TECHNICAL FIELD

The present invention relates to a composition for preventing or treating hearing loss, and more particularly to a pharmaceutical composition and a food composition for preventing or treating hearing loss, which contain a *Vitis vinifera* leaf extract as an active ingredient.

BACKGROUND ART

Hearing loss is a very common disorder which affects about 15 to 20% of the global population. The population suffering from hearing loss is further increasing due to environmental pollution and population aging in modern society. Since hearing impairment is permanent, its prevention is very important before its occurrence.

Hearing loss is mostly caused by environmental and genetic factors such as sudden, drug (antibiotic, anticancer drug), noise, traumatic, senile, and congenital factors, and hearing problems are mainly caused by sensorineural hearing loss characterized by auditory cell damage and death. For the treatment of sensorineural hearing loss, many signal pathway mechanisms involved in inner ear hair cell regeneration and hair cell proliferation and differentiation have been identified. In addition, along with the development of technologies such as gene editing or cell transplantation have been developed, great progress in the study of hair cell regeneration has been made in recent years. However, the development of a clear mechanism for suppression or prevention of hearing loss or agents for prevention and treatment of hearing loss is still insignificant (*Hanyang Med Rev*, vol 35(2); May 2015).

Recently, as the society is industrialized, the population suffering from hearing loss caused by noise is also increasing rapidly. Not only occupational noise-induced hearing loss in workers and soldiers working in noise environments, but also noise-induced hearing loss caused by cultural and leisure life is increasing. The Korean Industrial Accident Compensation Insurance Act stipulates that exposure to environmental noise above 90 dBA can damage hearing. The U.S. Occupational Safety and Health Administration (OSHA) has conducted noise management for noise environments above 85 dBA. Human hearing organs have been reported to be affected by noise above 75 dBA. Noise of 75 dBA is similar to the noise on the sides of vehicle roads, and thus it appears that all people in the industrial society live in environments with noise at a level harmful to hearing organs.

In addition to environmental noise, adolescents are frequently exposed to loud sounds in their free time, including the use of MP3, and thus noise-induced hearing loss has recently appeared in various age groups. Noise-induced hearing loss in younger days leads to hearing loss from the age of 40 so that conversation is only possible with hearing aids. When aging is accompanied, the degree of hearing loss becomes more severe. Assistive devices such as hearing aids are also less effective as the degree of hearing loss becomes severe, so that a severe degree of hearing loss causes serious problems in verbal communication. In other words, when the current young generation experiencing noise-induced hearing loss becomes elderly, the degree of hearing loss becomes more severe, and hearing loss has a significant effect on determination of the quality of life of various generations, from the elderly to the young.

Recently, as studies conducted to find effective substances for the prevention and treatment of hearing loss, preclinical studies on antioxidants, N-methyl-D-aspartate (NMDA) antagonists, apoptosis inhibitors, growth factors, etc. have been reported, but their progress to clinical trials has been limited (Prasher D., *Lancet,* 352, pp 1240-1242, 1998). To date, no drugs have been approved for the prevention and treatment of noise-induced hearing loss, and only drugs such as Mg, NAC (N-acetylcysteine) and Ebselen in the clinical stage and studies in the preclinical stage, have been reported to the academic community (Meister A., *Pharmacol. Ther.,* 51, pp 155-194, 1991; Attias J. et al., *Am. J. Otolaryngol.,* 15, pp 26-32, 1994; Yamasoba T. et al., *Neurosci. Lett.,* 380, pp 234-238, 2005).

Meanwhile, it has been disclosed that a grape leaf extract has an antioxidant effect, but it is not known that the grape leaf extract has the effect of preventing hearing loss (Korean Patent Publication No. 10-2010-0114349).

Accordingly, the present inventors have made extensive efforts to prevent and treat noise-induced hearing loss using natural products having excellent safety, and as a result, have found that a *Vitis vinifera* leaf extract effectively suppresses the increase in hearing threshold caused by noise or the like, thereby completing the present invention.

DISCLOSURE

Technical Problem

It is an object of the present invention to provide a pharmaceutical composition for preventing or treating hearing loss, which comprises a *Vitis vinifera* leaf extract as an active ingredient.

Another object of the present invention is to provide a food composition for preventing or ameliorating hearing loss, which comprises a *Vitis vinifera* leaf extract as an active ingredient.

Technical Solution

To achieve the above object, the present invention provides a pharmaceutical composition for preventing or treating hearing loss, which comprises a *Vitis vinifera* leaf extract as an active ingredient.

The present invention also provides a food composition for preventing or ameliorating hearing loss, which comprises a *Vitis vinifera* leaf extract as an active ingredient.

BRIEF DESCRIPTION OF THE DRAWINGS

The patent or application file of this patent contains at least one drawing executed in color. Copies of this patent with color drawing(s) will be provided by the Patent and Trademark Office upon request and payment of the necessary fee.

DETAILED DESCRIPTION AND EXEMPLARY EMBODIMENTS

Figure 1:
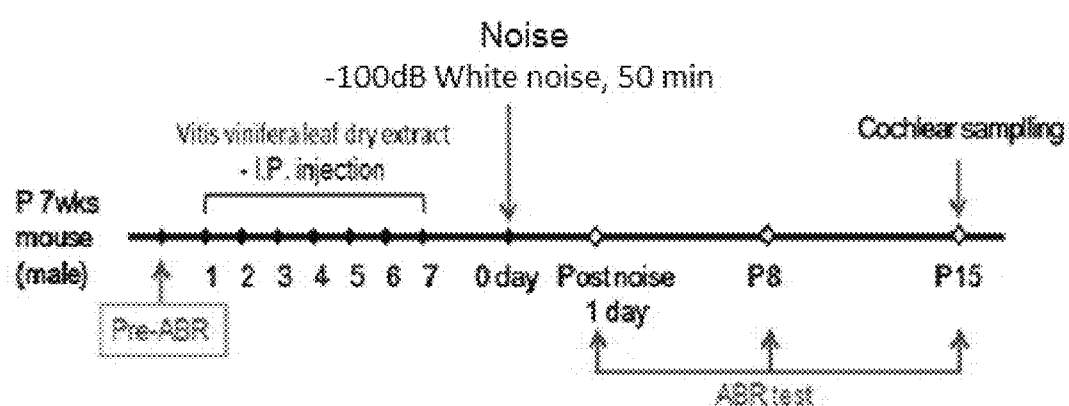
FIG. 1 is a schematic view showing an in vivo experiment using hearing loss mouse models.

Unless defined otherwise, all the technical and scientific terms used herein have the same meanings as commonly understood by one of ordinary skill in the art to which the invention pertains. Generally, the nomenclature used herein and the experiment methods, which will be described below, are those well-known and commonly employed in the art.

In the present invention, a hearing loss mouse model was established, and then treated with a *Vitis vinifera* leaf extract, and the changes in auditory function and morphology caused by noise exposure were analyzed. As a result, it was confirmed that the hearing threshold of the mouse model treated with the *Vitis vinifera* leaf extract significantly decreased compared to that of the mouse model not treated with the *Vitis vinifera* leaf extract, and the expression level of antioxidant enzyme in the cochlear spiral ganglion and auditory hair cells of the mouse model treated with the *Vitis vinifera* leaf extract increased. In addition, it was confirmed that when an auditory cell line treated with the *Vitis vinifera* leaf extract was treated with hydrogen peroxide, cytotoxicity and cell death was inhibited and the mRNA and protein expressions of catalase and superoxide dismutase 2 (SOD2) increased, compared to when the auditory cell line was not treated with *Vitis vinifera* leaf extract. This suggests that the *Vitis vinifera* leaf extract is effective in preventing or treating noise-induced hearing loss. In addition, it was confirmed that in the cell line treated with the *Vitis vinifera* leaf dry extract, the cytotoxicity and cell death caused by reactive oxygen species was inhibited.

Therefore, in one aspect, the present invention is directed to a pharmaceutical composition for preventing or treating hearing loss, comprising a *Vitis vinifera* leaf extract as an active ingredient.

As used herein, the term "extract" refers to a substance obtained by extraction from *Vitis vinifera* leaves.

In the present invention, the *Vitis vinifera* leaf extract may be obtained by extracting *Vitis vinifera* leaves with a solvent selected from the group consisting of water, a C1 to C4 alcohol, and a mixed solvent of water and a C1 to C4 alcohol. Preferably, the *Vitis vinifera* leaf extract of the present invention may be obtained by extracting *Vitis vinifera* leaves with water as a solvent.

As the mixed solvent, preferably, an about 70% ethanol aqueous solution may be used. The extraction may be performed by an extraction method known in the art, for example, macerating, hot-water extraction, ultrasonic extraction, or reflux cooling extraction, but is not limited thereto. As the extraction temperature, various extraction temperatures appropriate for the extraction method selected may be employed by a person of ordinary skill in the art. For example, the extraction may be performed at a temperature ranging from 20° C. to 100° C., but is not limited thereto. In addition, the extraction time may vary depending on the extraction method, and may be appropriately selected by a person of ordinary skill in the art. For example, the extraction may be performed one or multiple times within the range of about 1 hour to 10 days, but is not limited thereto. Preferably, the extraction may be performed by extracting with the extraction solvent two or three times at about 2-day intervals at room temperature.

The *Vitis vinifera* leaf extract of the present invention contains polyphenol as an active ingredient.

As used herein, the term "polyphenols" refers to compounds having two or more aromatic hydroxyl groups, which have a high antioxidant activity that protects DNA from being damaged by exposure to reactive oxygen species in vivo or protects cell proteins and enzymes, thus reducing the risk of various diseases. In addition to already widely known antioxidant effects, the polyphenols are effective in ameliorating symptoms that may be caused by circulatory failure. In addition, polyphenols are known to be effective in eliminating swelling and discomfort caused by lower limb venous insufficiency because they act on the blood vessels to increase the elasticity of the blood vessel wall and regulate capillary permeability to promote circulation.

In the present invention, the pharmaceutical composition may comprise one or more substances selected from the group consisting of a Korean red-*ginseng* extract, a *Ginkgo biloba* leaf extract, and resveratrol.

In the present invention, the hearing loss may be sensorineural hearing loss, and the sensorineural hearing loss may comprise noise-induced hearing loss, ototoxic hearing loss, sudden sensory neural hearing loss, and presbycusis.

As used herein, the term "hearing loss" refers to a condition in which hearing is reduced due to abnormalities in any part of the outer ear, the middle ear, and nerve-conduction pathways, and includes conductive hearing loss and sensorineural hearing loss. Preferably, the hearing loss in the present invention includes conductive hearing loss caused by various factors such as noise, drugs, aging, trauma, and viruses, and sensorineural hearing loss including noise-induced hearing loss (NIHL) showing symptoms of damage to the cochlea and auditory nerves due to various noises.

The noise-induced hearing loss comprises Acoustic Trauma Hearing loss, Temporary threshold shift (TTS) caused by a short-term noise, Permanent threshold shift (PTS) caused by a long-term noise.

The *Vitis vinifera* leaf extract or polyphenol of the present invention can suppress hearing loss, in particular, acoustic trauma, temporary or permanent noise-induced hearing loss by effectively inhibiting an increase in the hearing threshold caused by noise and the likes.

Figure 2:
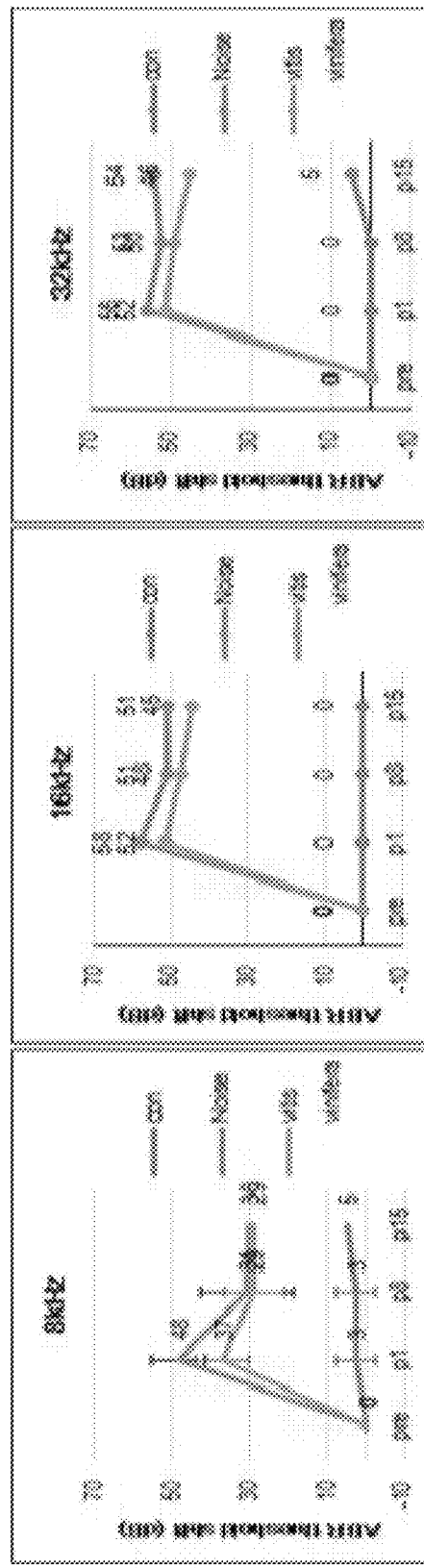
FIG. 2 shows the results of measuring auditory brainstem response (ABR) to observe the change in hearing threshold caused by a *Vitis vinifera* leaf dry extract.
Figure 3:
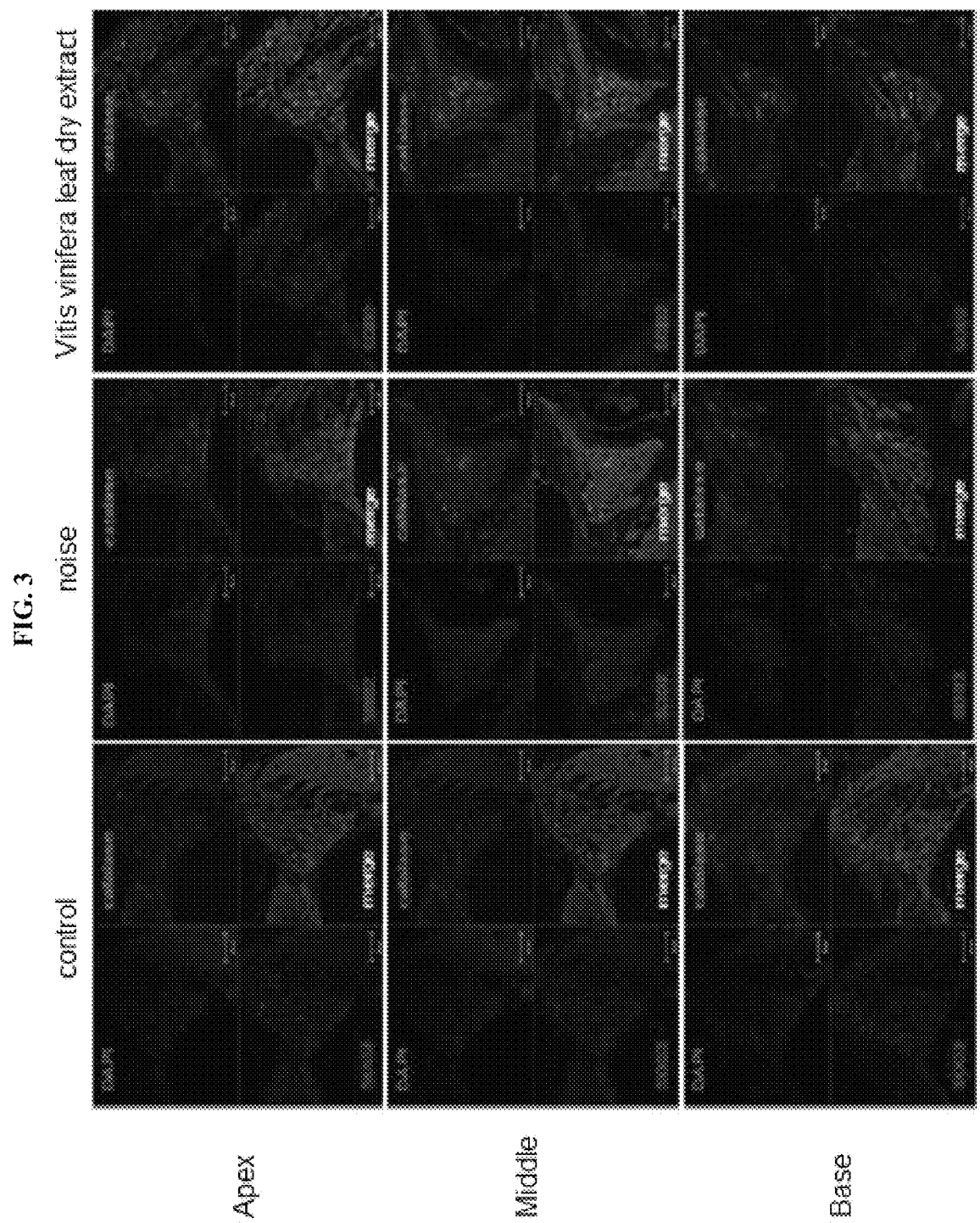
FIG. 3 shows the results of performing immunostaining to observe the antioxidant effect of a *Vitis vinifera* leaf dry extract in cochlear spiral ganglion.
Figure 4:
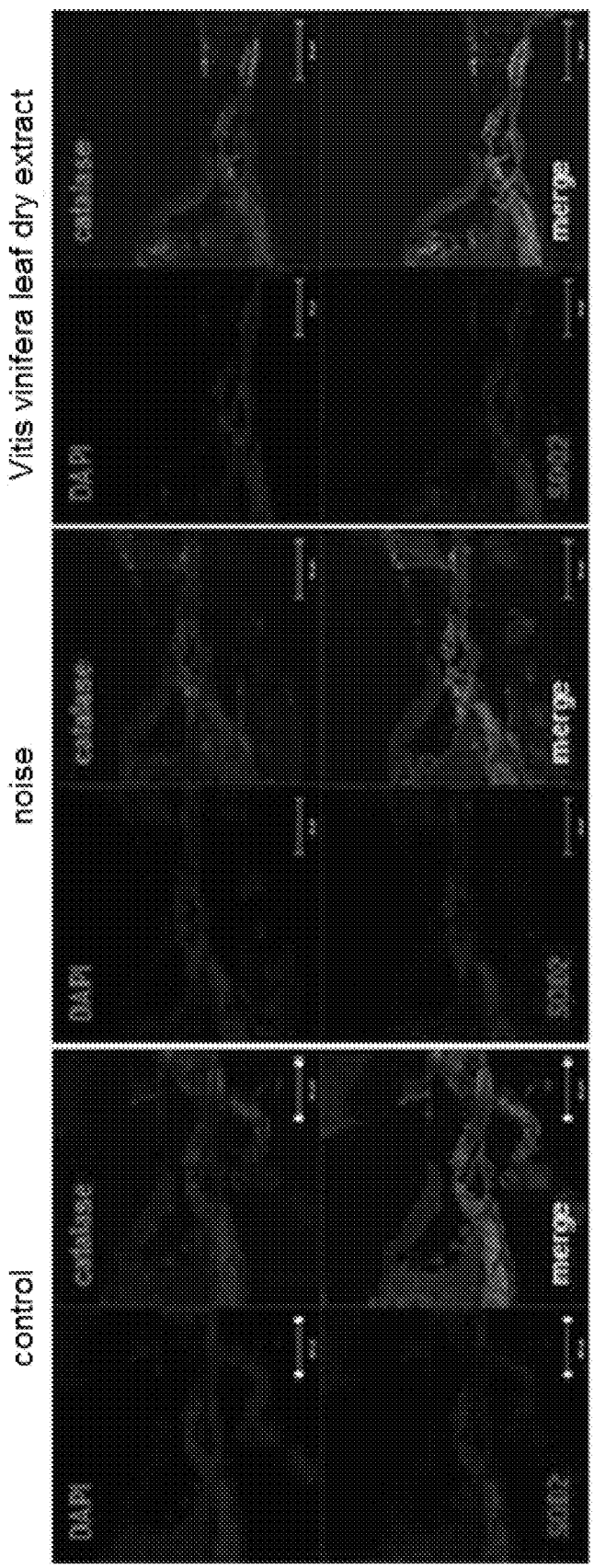
FIG. 4 shows the results of performing immunostaining to observe the antioxidant effect of a *Vitis vinifera* leaf dry extract in cochlear auditory hair cells.

In one Example, the *Vitis vinifera* leaf dry extract of the present invention was lyophilized and used and stored in powder form. The powder was dissolved in water and administered to each mouse at a dose of 80 mg/kg, and then auditory brainstem response (ABR) testing was performed to observe the change in hearing threshold caused by noise exposure. As a result, it was confirmed that the hearing threshold of the mice treated with the *Vitis vinifera* leaf dry extract significantly decreased compared to that of the control group (FIG. 2). In addition, when noise exposure, the expressions of antioxidant enzyme in the cochlear spiral ganglion and auditory hair cells of the group treated with the *Vitis vinifera* leaf dry extract and the untreated group were observed, and as a result, it was confirmed that the expression of antioxidant enzyme in the group treated with the *Vitis vinifera* leaf dry extract significantly increased (FIGS. 3 and 4).

Figure 5:
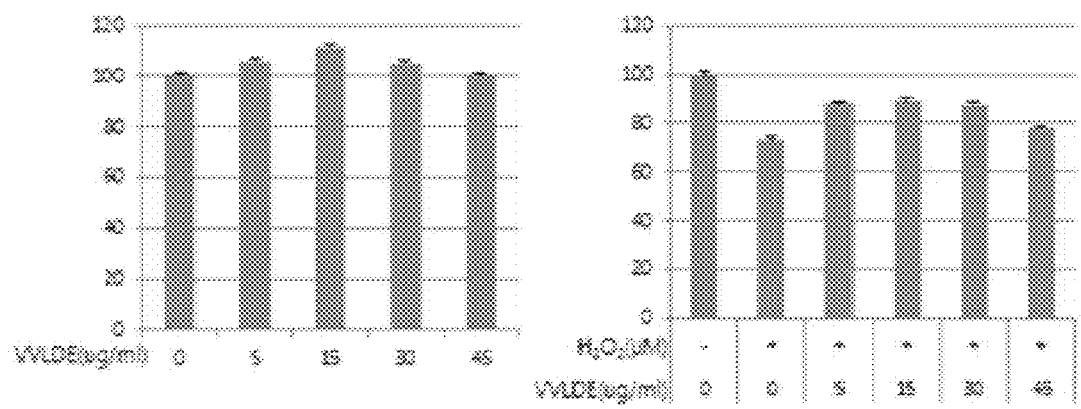
FIG. 5 shows the results of performing WST-1 assay to examine cytotoxicity of an auditory cell line treated with a *Vitis vinifera* leaf dry extract.
Figure 6:
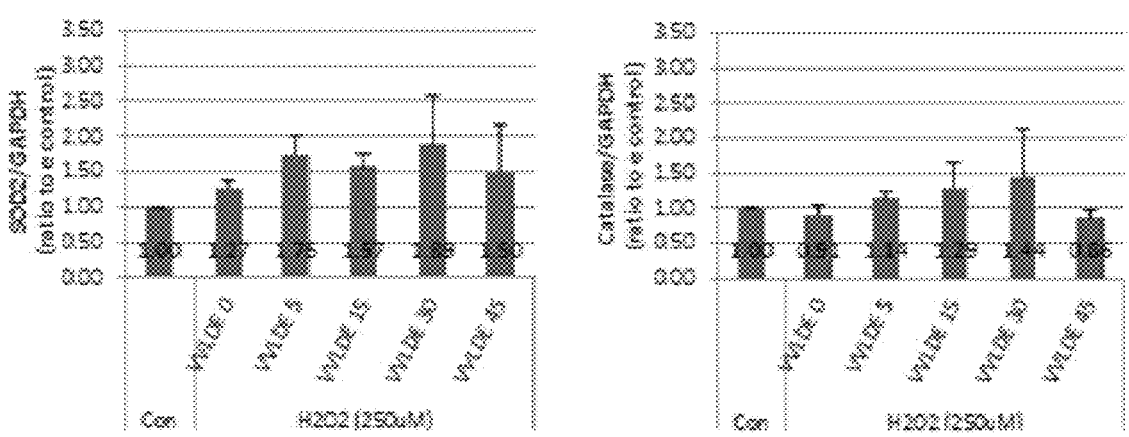
FIG. 6 shows the results of performing quantitative real-time PCR to observe the mRNA expression of antioxidant enzyme in auditory cells treated with a *Vitis vinifera* leaf dry extract.
Figure 7:
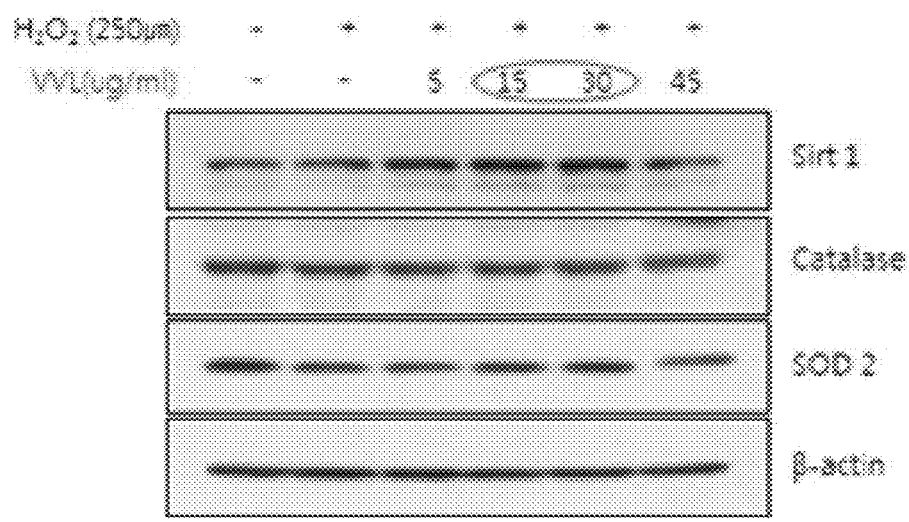
FIG. 7 shows the results of performing Western blotting to observe the protein expression of antioxidant enzyme in auditory cells treated with a *Vitis vinifera* leaf dry extract.

In one Example of the present invention, in order to generate reactive oxygen species (ROS) caused by oxidative stress during noise-induced hearing loss, the auditory cell line pretreated with each of 5 µg/ml, 15 µg/ml, 30 µg/ml and 45 µg/ml of the *Vitis vinifera* leaf dry extract was treated with hydrogen peroxide ($H_2O_2$), and then observation of cytotoxicity and cell death in the auditory cell line was performed. As a result, it was observed that cytotoxicity and cell death were inhibited (FIG. 5). In addition, it was confirmed that the mRNA and protein expressions of catalase and superoxide dismutase 2 (SOD2) were increased (FIGS. 6 and 7).

Figure 8:
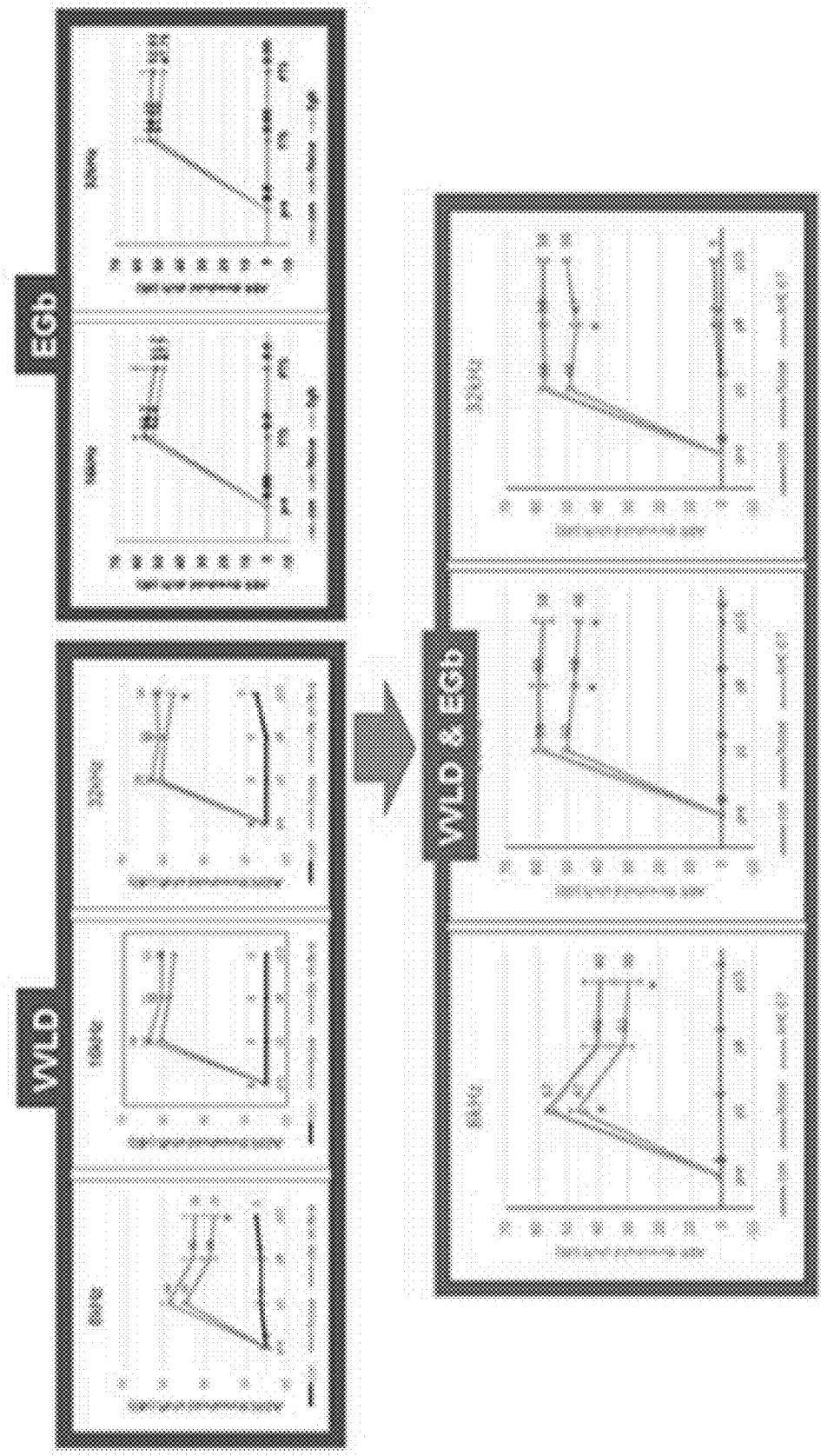
FIG. 8 shows the results of measuring auditory brainstem response (ABR) to observe the change in hearing threshold caused by treatment with a combination of a *Vitis vinifera* leaf dry extract and a *Ginkgo biloba* leaf extract.

In one Example of the present invention, auditory brainstem response (ABR) testing was performed to observe the change in hearing threshold caused by noise exposure in control groups administered with the *Vitis vinifera* leaf dry extract of the present invention or a *Ginkgo biloba* leaf extract respectively and a test group co-administered with the two extracts (60 mg/kg of the *Vitis vinifera* leaf dry extract, and 3.5 mg/kg of the *Ginkgo biloba* leaf extract). As a result, the hearing threshold of the mice co-administered with the *Vitis vinifera* leaf dry extract and the *Ginkgo biloba* leaf extract significantly was decreased compared to that of the control groups (FIG. 8).

As described above, the *Vitis vinifera* leaf extract of the present invention significantly decreases the hearing threshold, increases the expression level of antioxidant enzyme in the cochlear spiral ganglion and auditory hair cells, and inhibits cytotoxicity and cell death, so that it can be used for the prevention or treatment of hearing loss.

As used herein, the term "reactive oxygen" refers to free radicals derived from oxygen. These reactive oxygen induce lipid peroxidation, DNA damage, protein oxidation, etc., by reaction with proteins, lipids, carbohydrates and the like, causing damage to intracellular structures, resulting in cell death.

Oxygen-related toxic substances in the human body are referred to as reactive oxygen species (ROS). The ROS include free radicals such as superoxide, hydroxyl, peroxyl, alkoxyl, and hydroperoxyl, and non-free radicals such as hydrogen peroxide, hypochlorous acid, ozone, singlet oxygen, and peroxinitrite.

In another aspect, the present invention is directed to a method for preventing or treating hearing loss by use of a pharmaceutical composition comprising a *Vitis vinifera* leaf extract.

The composition of the present invention is administered in a pharmaceutically effective amount. As used herein, the term "pharmaceutically effective amount" refers to an amount sufficient to treat diseases at a reasonable benefit/risk ratio applicable to any medical treatment. The effective dosage level of the composition may be determined depending on the subject's type, the disease severity, the subject's age and sex, the activity of the drug, sensitivity to the drug, the duration of administration, the route of administration, excretion rate, the duration of treatment, factors including drugs used in combination with the composition, and other factors known in the medical field. The pharmaceutical composition of the present invention may be administered as an individual therapeutic agent or in combination with other therapeutic agents, and may be administered sequentially or simultaneously with conventional therapeutic agents. The composition can be administered in a single or multiple dosage form. It is important to administer the composition in the minimum amount that can exhibit the maximum effect without causing side effects, in view of all the above-described factors, and this amount can be easily determined by a person skilled in the art.

The pharmaceutical composition according to the present invention may comprise a pharmaceutically acceptable carrier, and can be formulated according to a conventional method. For example, it may be formulated in the form of powders, granules, tablets, capsules, suspensions, emulsions, syrups, aerosols, and the like for oral applications, agents for external applications, suppositories, and sterile injection solutions.

Examples of the pharmaceutically acceptable carrier may include, but are not limited to, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oil, which are is generally used in the art to which the present invention pertains. In addition, the pharmaceutical composition according to the present invention comprises diluents or excipients, such as fillers, extenders, binders, wetting agents, disintegrants or surfactants, and other pharmaceutically acceptable additives.

When the pharmaceutical composition of the present invention is formulated as a solid formulation for oral administration, the solid formulations include tablets, pills, powders, granules, capsules, etc. Such solid formulations may include at least one excipient, such as starch, calcium carbonate, sucrose, lactose, gelatin, etc., and include, but not limited to, lubricants such as magnesium stearate, and talc.

When the pharmaceutical composition of the present invention is formulated as a liquid formulation for oral administration, the liquid formulations include suspensions, internal solutions, emulsions, syrups, etc. Such liquid formulations may include diluents such as water, liquid paraffin, etc., and include, but not limited to, wetting agents, sweeteners, aromatics, preservatives, etc.

When the pharmaceutical composition of the present invention is formulated as a formulation for parenteral administration, the formulations for parenteral administration include sterilized aqueous solutions, non-aqueous solvents, suspensions, emulsions, lyophilized agents, and suppositories. Non-aqueous solvents and suspensions include, but not limited to, propylene glycol, polyethylene glycol, vegetable oils such as olive oil, or injectable esters such as ethyloleate. As a base for suppositories, Witepsol, Macrogol, Tween 61, cacao fat, laurin fat, glycerogelatin, etc. may be used, but is not limited thereto.

The pharmaceutical composition according to the present invention may be administered orally, or parenterally (for example, intravenously, subcutaneously, intraperitoneally, or topically) according to a desired purpose. The preferred dosage of the composition of the present invention varies depending on various factors, including the patient's condition and weight, the severity of disease, the type of drug, the route and period of administration, but can be suitably determined by a person skilled in the art.

The preferred dosage of the *Vitis vinifera* leaf extract contained in the pharmaceutical composition of the present invention varies depending on various factors, including the patient's condition, weight and age, the severity of disease, the type of drug, the route and period of administration, but can be suitably determined by a person skilled in the art. For example, the *Vitis vinifera* leaf extract of the present invention may be administered at a daily dose of from 1 to 2,000 mg/kg, and preferably 10 to 2,000 mg/kg. The *Vitis vinifera* leaf extract may be administered in a single dose or in multiple doses per day. The dosage is not intended to limit the present invention in any way.

In still another aspect, the present invention is directed to a food composition for preventing or ameliorating hearing loss, comprising a *Vitis vinifera* leaf extract as an active ingredient.

In the present invention, the *Vitis vinifera* leaf extract may be obtained by extracting *Vitis vinifera* leaves with a solvent selected from the group consisting of water, a C1 to C4 alcohol, and a mixed solvent of water and a C1 to C4 alcohol.

In the present invention, the pharmaceutical composition may comprise one or more substances selected from the group consisting of a Korean red-*ginseng* extract, a *Ginkgo biloba* leaf extract, and resveratrol.

In the present invention, the hearing loss may be sensorineural hearing loss, and the sensorineural hearing loss may comprise noise-induced hearing loss, ototoxic hearing loss, sudden sensory neural hearing loss, and presbycusis.

The food composition of the present invention can be used as a health functional food. As used herein, the term "health functional food" refers to a food which is prepared and processed from raw materials or components having functionality useful for the human body pursuant to the law No. 6722 on the health functional food, or the term "functionality" refers to taking a food for the purpose of controlling nutrients with respect to the structure and function of the human body or obtaining the effects useful for the health purposes such as physiologically functional purpose.

The food composition of the present invention may comprise a conventional food additive, and the suitability of the "food additive" is judged by standards and criteria on the relevant item according to the general regulations and general test methods of the Food Additives Code, approved by the Korean Ministry of Food and Drug Safety, unless otherwise specified.

Items listed in the Food Additives Code include, for example, chemical synthetic products such as ketones, glycine, potassium citrate, nicotinic acid and cinnamic acid; natural additives such as persimmon color, licorice extract, crystalline cellulose, Kaoliang color, and guar gum; and mixed agents such as a sodium L-glutamate agent, a noodles-added alkaline agent, a preservative agent, and a tar coloring agent.

The food composition of the present invention may contain a *Vitis vinifera* leaf extract in an amount of 0.01 to 95 wt %, preferably 1 to 80 wt %, based on the total weight of the composition for the purpose of preventing and/or ameliorating hearing loss, particularly noise-induced hearing loss.

In addition, the food composition of the present invention may be prepared and processed in the form of tablet, capsule, powder, granule, liquid or pill for the purpose of preventing and/or ameliorating hearing loss.

For example, a health functional food in the form of tablet may be prepared by granulating a mixture of the *Vitis vinifera* leaf extract, an excipient, a binder, a disintegrant and other additives according to a conventional method, and then compression-molding the mixture after addition of a lubricant or the like, or directly compression-molding the mixture. In addition, health functional foods other than the tablet form may contain a flavor enhancer or the like, if necessary, and may be coated with a suitable coating agent, if necessary.

Among health functional foods in the form of capsule, a hard capsule formulation may be prepared by filling into a conventional hard capsule a mixture of the *Vitis vinifera* leaf extract and additives such as an excipient, or granules or coated granules thereof, and a soft capsule formulation may be prepared by filling a mixture of the *Vitis vinifera* leaf extract and additives such as an excipient into a capsule base such as gelatin. The soft capsule formulation may, if necessary, contain a plasticizer such as glycerin or sorbitol, a coloring agent, a preservative, etc.

A health functional agent in the form of pill may be prepared by molding a mixture of the *Vitis vinifera* leaf extract, an excipient, a binder, a disintegrant and the like according to a suitable method, and may, if necessary, be coated with white sugar or other suitable coating agent, or be coated with starch, talc or a suitable substance.

A health functional food in the form of granule may be prepared by granulating a mixture of the *Vitis vinifera* leaf extract, an excipient, a binder, a disintegrant and the like according to a suitable method, and may, if necessary, contain a fragrance ingredient, a flavor enhancer or the like. The health functional food in the form of granule may have a particle size distribution as follows when measuring the particle size using a No. 12 sieve (1680 μm), a No. 14 sieve (1410 μm) and a No. 45 sieve (350 μm): 100% of the total amount passes through the No. 12 sieve, 5.0% or less of the total amount is retained on the No. 14 sieve, and 15.0% or less of the total amount passes through the No. 45 sieve.

The above-mentioned excipient, binder, disintegrant, lubricant, flavor enhancer and fragrance ingredient may be defined as corresponding materials having the same or similar functions disclosed in references known in the art (The Korean pharmacopoeia review, Moonsungsa Publication Co., Korea Pharmaceutical University Association, Fifth edition, p 33-48, 1989).

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: In Vivo Experiment—Evaluation of Hearing Loss Preventive Effect by Auditory Function Analysis Using Noise-Induced Hearing Loss Mouse Model Auditory brainstem response (ABR) testing was performed for a total of twenty four 7-week-old male Balb/c mice, and mice with congenital abnormal hearing were excluded.

Before noise exposure, the mice were divided into a test group administered with a *Vitis vinifera* leaf dry extract at a dose of 80 mg/kg and a control group not administered with the *Vitis vinifera* leaf dry extract. Each of the groups consisted of 12 mice. The test group was administered intraperitoneally with the *Vitis vinifera* leaf dry extract once a day for 7 days. After administration, the mice were exposed to white noise (100 dB) for 50 minutes to induce noise-induced hearing loss.

After 7 days of administration with the *Vitis vinifera* leaf dry extract, auditory brainstem response (ABR) testing was performed to analyze auditory function for the noise-induced hearing loss. Using a TDT ABR device, tone burst sounds of 8 kHz, 16 kHz and 32 kHz were applied, and the lowest stimulus sound intensity (dB) that evoked the waveform of wave V was expressed as hearing threshold, and the effect of preventing noise-induced hearing loss was comparatively analyzed by measuring the hearing of the test group administered with the drug and the hearing of the control group before noise exposure.

As a result, both the test group and the control group showed increased hearing threshold on 1, 7 and 14 days after noise exposure. However, it was observed that the hearing threshold of the test group pretreated with the *Vitis vinifera* leaf dry extract significantly was decreased compared to that of the control group (FIG. 2). Thus, it can be seen that the *Vitis vinifera* leaf dry extract prevents noise-induced hearing loss.

Example 2: In Vivo Experiment—Evaluation of Hearing Loss Preventive Effect by Morphological Analysis Using Noise-Induced Hearing Loss Mouse Model After the mice of Example 1 were exposed to noise, the expressions of antioxidant enzymes in the cochlear spiral ganglion of the group treated with the *Vitis vinifera* leaf dry extract and the untreated group were analyzed by immunostaining. As a result, it was observed that the expression of antioxidant enzyme in the group treated with the *Vitis vinifera* leaf dry extract significantly was increased (FIG. 3).

In addition, the expressions of antioxidant enzymes in the cochlear auditory hair cells of the group treated with the *Vitis vinifera* leaf dry extract and the untreated group were analyzed by immunostaining. As a result, it was observed that the expression of antioxidant enzyme in the group treated with the *Vitis vinifera* leaf dry extract significantly was increased (FIG. 4).

Thus, it can be seen that the *Vitis vinifera* leaf dry extract prevents noise-induced hearing loss.

Example 3: In Vitro Experiment—Cell Death of Auditory Cells by *Vitis vinifera* Leaf Dry Extract For an in vitro cell experiment, an auditory cell line (HEI-OC1; House-Ear Institute-organ of Corti 1) expressing auditory genes was cultured.

To evaluate cell death, the auditory cell line was divided into groups pretreated with each of 5 μg/ml, 15 μg/ml, 30 μg/ml and 45 μg/ml of the *Vitis vinifera* leaf dry extract and an untreated group. Thereafter, the auditory cell line was treated with hydrogen peroxide ($H_2O_2$), and then the cytotoxicity and cell death effects by the hydrogen peroxide were analyzed by WST-1 assay. As a result, it was observed that cytotoxicity and cell death of the auditory cell line of the group pretreated with the *Vitis vinifera* leaf dry extract was inhibited. In particular, it was confirmed that when the auditory cell line was treated with 15 μg/ml of the *Vitis vinifera* leaf dry extract, cytotoxicity and cell death of the auditory cell line were inhibited (FIG. 5).

Example 4: In Vitro Experiment—Antioxidant Activity of *Vitis vinifera* Leaf Dry Extract To observe the antioxidant activity in the auditory cells treated with the *Vitis vinifera* leaf dry extract, the cell line of Example 3 was divided into groups pretreated with each of 5 μg/ml, 15 μg/ml, 30 μg/ml and 45 μg/ml and an untreated group, and then the cell lines were treated with hydrogen peroxide. Thereafter, western blotting and quantitative real-time PCR were performed using catalase and superoxide dismutase 2 (SOD2) antibodies.

As a result, it was observed that the mRNA and protein expressions of catalase and superoxide dismutase 2 (SOD2) in the groups treated with the *Vitis vinifera* leaf dry extract were increased. In particular, it was confirmed that when the auditory cells were treated with 15 μg/ml or 30 μg/ml of the *Vitis vinifera* leaf dry extract, the mRNA and protein expressions of catalase and superoxide dismutase 2 (SOD2) were significantly increased (FIGS. 6 and 7).

Through the results of the experiments performed using the auditory cell line and the noise-induced hearing loss model, it can be seen that the *Vitis vinifera* leaf dry extract is useful for preventing and treating hearing loss.

Example 5: In Vivo Experiment—Evaluation of Hearing Loss Preventive Effect of Combination of *Vitis vinifera* Leaf Dry Extract with *Ginkgo Biloba* Leaf Extract by Auditory Function Analysis Using Noise-Induced Hearing Loss Mouse Model Before the mice of Example 1 were exposed to noise, the mice were divided into control groups administered with each of the *Vitis vinifera* leaf dry extract and a *Ginkgo biloba* leaf extract and a test group co-administered with the two extracts (60 mg/kg of the *Vitis vinifera* leaf dry extract, and 3.5 mg/kg of the *Ginkgo biloba* leaf extract). Each of the groups consisted of 12 mice. The test group was co-administered intraperitoneally with 60 mg/kg of the *Vitis vinifera* leaf dry extract and 3.5 mg/kg of the *Ginkgo biloba* leaf extract once a day for 7 days. After administration, the mice were exposed to white noise (100 dB) for 50 minutes to induce noise-induced hearing loss.

After 7 days of administration with the *Vitis vinifera* leaf dry extract, auditory brainstem response (ABR) testing was performed to analyze auditory function for the noise-induced hearing loss. Using a TDT ABR device, tone burst sounds of 8 kHz, 16 kHz and 32 kHz were applied, and the effect of preventing noise-induced hearing loss was comparatively analyzed by measuring the hearing of the test group and the hearing of the control groups before noise exposure.

As a result, the test group and the control groups all showed increased hearing threshold on 1, 7 and 14 days after noise exposure. However, it was observed that the hearing threshold of the test group pretreated with the combination of the extracts significantly was decreased compared to that of the control groups (FIG. 8). Thus, it can be seen that co-administration of the *Vitis vinifera* leaf dry extract and the *Ginkgo biloba* extract prevents noise-induced hearing loss compared to administration of each of the extracts.

INDUSTRIAL APPLICABILITY

The pharmaceutical composition for preventing or treating hearing loss comprising a *Vitis vinifera* leaf extract as an active ingredient according to the present invention can protect cochlear auditory hair cells and spiral ganglion cells from being damaged by noise or the like, and can effectively reduce the hearing threshold measured in auditory nerve. Thus, it will be useful for preventing or treating hearing loss.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of treating hearing loss in a human in need thereof consisting essentially of administering to the human in need thereof a therapeutically effective amount of a *Vitis vinifera* leaf extract to effectively treat the hearing loss in the human in need thereof, wherein the *Vitis vinifera* leaf extract is the only active ingredient in the method and wherein the hearing loss is selected from the group consisting of noise-induced hearing loss, ototoxic hearing loss, sudden sensory neural hearing loss, and presbycusis.

2. The method of claim 1, wherein the *Vitis vinifera* leaf extract is obtained by extracting *Vitis vinifera* leaves with a solvent selected from the group consisting of water, a C1 to C4 alcohol, and a mixed solvent of water and a C1 to C4 alcohol.

3. A method of treating hearing loss in a human in need thereof consisting essentially of administering to the human in need thereof a mixture of therapeutically effective amounts of *Vitis vinifera* leaf extract and at least one of Korean red-*ginseng* extract or *Ginkgo biloba* leaf extract to effectively treat the hearing loss in the human in need thereof.

4. The method of claim 3, wherein the *Vitis vinifera* leaf extract is obtained by extracting *Vitis vinifera* leaves with a solvent selected from the group consisting of water, a C1 to C4 alcohol, and a mixed solvent of water and a C1 to C4 alcohol.

5. The method of claim 3, wherein the hearing loss is selected from the group consisting of noise-induced hearing loss, ototoxic hearing loss, sudden sensory neural hearing loss, and presbycusis.

* * * * *